(12) United States Patent
Ben Arie et al.

(10) Patent No.: US 11,253,236 B2
(45) Date of Patent: Feb. 22, 2022

(54) NEEDLE-HANDLING DEVICE

(71) Applicant: ONEPASS MEDICAL LTD., Katzrin (IL)

(72) Inventors: Jacob Ben Arie, Haifa (IL); Jesse Lachter, Haifa (IL)

(73) Assignee: ONEPASS MEDICAL LTD., Katzrin (IL)

( * ) Notice: Subject to any disclaimer, the term of this patent is extended or adjusted under 35 U.S.C. 154(b) by 44 days.

(21) Appl. No.: 17/021,681

(22) Filed: Sep. 15, 2020

(65) Prior Publication Data

US 2021/0113197 A1 Apr. 22, 2021

Related U.S. Application Data

(60) Provisional application No. 62/924,072, filed on Oct. 21, 2019.

(51) Int. Cl.
*A61B 10/02* (2006.01)
*A61B 17/34* (2006.01)

(52) U.S. Cl.
CPC ...... *A61B 10/0266* (2013.01); *A61B 17/3403* (2013.01); *A61B 17/3421* (2013.01);
(Continued)

(58) Field of Classification Search
CPC ............ A61B 10/0266; A61B 17/3403; A61B 17/3496; A61B 17/3421; A61B 2017/345; A61B 2017/3484
See application file for complete search history.

(56) References Cited

U.S. PATENT DOCUMENTS 5,409,012 A 4/1995 Sahatjian
5,415,182 A 5/1995 Chin et al.
(Continued)

FOREIGN PATENT DOCUMENTS

EP 0450886 B1 10/1991
EP 1251781 B1 12/2006
(Continued)

OTHER PUBLICATIONS

LeBlanc JK et al, "Optimal number of EUS-guided fine needle passes needed to obtain a correct diagnosis", Gastrointest Endosc 2004;59:475-81.

*Primary Examiner* — Anh T Dang
(74) *Attorney, Agent, or Firm* — The Roy Gross Law Firm, LLC; Roy Gross

(57) ABSTRACT

An apparatus comprising: a sheath comprising a plurality of openings at a distal end; an elongate first needle extendible perpendicularly from said sheath through one of said plurality of openings; and an assembly comprising at least two second needles arranged in a predetermined pattern relative to said first needle, and extendible perpendicularly from said sheath, wherein, when extended from said distal end of said sheath: (i) each of said second needles extends a different length from said distal end of said sheath, (ii) at least a distal portion of each of said second needles is resiliently biased to extend laterally outwardly in relation to said first needle, and (iii) a lateral spread region defined by said distal portions of all of said second needles is determined based, at least in part, on a distance of said extending from said distal end of said sheath.

18 Claims, 14 Drawing Sheets

(52) U.S. Cl.
CPC .... *A61B 17/3496* (2013.01); *A61B 2017/345* (2013.01); *A61B 2017/3484* (2013.01)

(56) References Cited

U.S. PATENT DOCUMENTS

| | | |
|---|---|---|
| 6,730,061 B1 | 5/2004 | Cuschieri et al. |
| 2001/0001811 A1 | 5/2001 | Burney et al. |
| 2002/0026127 A1 | 2/2002 | Balbierz et al. |
| 2002/0120238 A1 | 8/2002 | McGuckin et al. |
| 2002/0188275 A1 | 12/2002 | McGuckin |
| 2003/0195436 A1 | 10/2003 | Van Bladel et al. |
| 2004/0068242 A1 | 4/2004 | McGuckin |
| 2004/0260274 A1 | 12/2004 | Hardin et al. |
| 2005/0228312 A1 | 10/2005 | Surti |
| 2006/0116605 A1 | 6/2006 | Nakao |
| 2006/0167416 A1 | 7/2006 | Mathis et al. |
| 2007/0162061 A1 | 7/2007 | Way et al. |
| 2007/0270710 A1 | 11/2007 | Frass et al. |
| 2008/0071193 A1* | 3/2008 | Reuber ............... A61B 10/0283 600/567 |
| 2009/0287114 A1 | 11/2009 | Lee et al. |
| 2010/0298736 A1 | 11/2010 | Leny |
| 2011/0130680 A1 | 6/2011 | Dahlstrand |
| 2012/0010527 A1 | 1/2012 | Sundheimer et al. |
| 2015/0087994 A1 | 3/2015 | Matsuno et al. |
| 2015/0164487 A1 | 6/2015 | Mugan et al. |
| 2016/0000415 A1* | 1/2016 | Belsky ............... A61B 10/0233 600/567 |
| 2016/0331468 A1* | 11/2016 | Lee ................... A61B 17/3403 |
| 2019/0021707 A1 | 1/2019 | Belsky et al. |
| 2019/0090862 A1 | 3/2019 | O'Callaghan et al. |

FOREIGN PATENT DOCUMENTS

| | | |
|---|---|---|
| WO | 2000033909 A1 | 6/2000 |
| WO | 2000064526 A1 | 11/2000 |
| WO | 2010014034 A1 | 2/2010 |
| WO | 2014136045 A1 | 9/2014 |
| WO | 2017037720 A1 | 3/2017 |

* cited by examiner

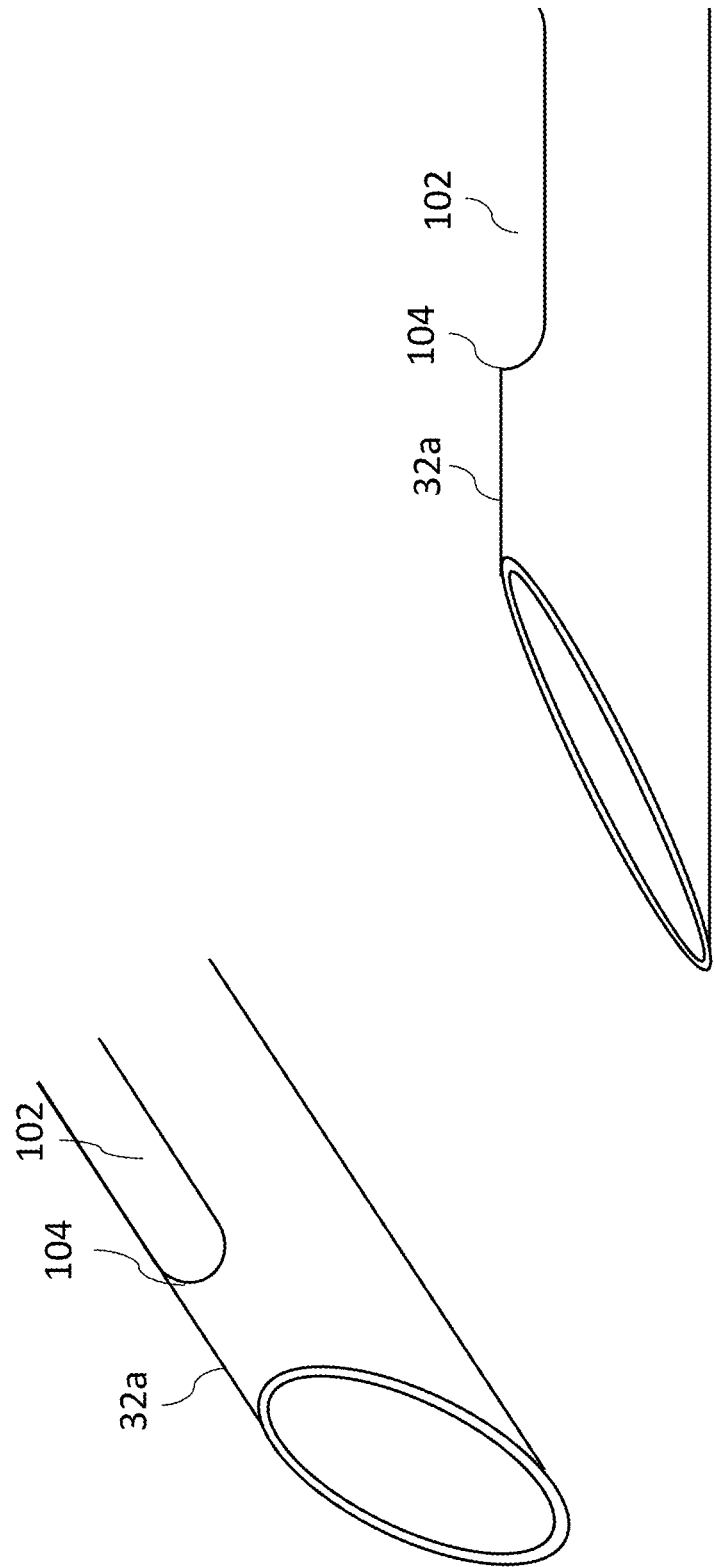

NEEDLE-HANDLING DEVICE

CROSS REFERENCE TO RELATED APPLICATIONS

This application claims the benefit of priority of U.S. Provisional Patent Application No. 62/924,072, filed Oct. 21, 2019, entitled "Needle-Handling Device," which is incorporated herein by reference in its entirety.

FIELD OF THE INVENTION

Some embodiments of the present invention relate in general to tissue sampling. More specifically, some embodiments of the present invention relate to tissue-sampling using Fine Needle Aspiration (FNA) biopsy.

BACKGROUND OF THE INVENTION

Tissue/fluid sampling (e.g., for biopsy) is used in many medical fields, e.g., to help in diagnosing of conditions. Physicians (e.g., gastroenterologists) sometimes use an endoscope when performing a biopsy, e.g., in order to sample tissue that cannot easily be reached percutaneously, or to which the physician does not have line-of-sight. Fine-needle aspiration biopsy (FNAB, FNA or NAB), or fine-needle aspiration cytology (FNAC), is a common diagnostic procedure used to investigate superficial lumps or masses. A fine needle is used to obtain a small sample of tissue; sufficient for examination of cells from the body under a microscope (cytology examination). EUS-FNA is fine needle aspiration during endoscopic ultrasound, using an ultrasound equipped endoscope to navigate to and identify the tissue (e.g., a lesion), and to guide a needle into the tissue.

However, the capability of these procedures to efficiently obtain samples sufficient for diagnostic and/or prognostic analysis remains limited relative to diagnostic needs. It is often necessary to take multiple samples of the tissue in order to increase diagnostic accuracy and reliability, since a single sample may not represent the entirety of the tissue or lesion from which the sample is extracted.

Inadequate biopsy samples often require repeated biopsy procedures and lead to a delay in diagnosis resulting in a delay in treatment. In addition, inadequate biopsy procedures add a burden to the healthcare system resulting in considerable incremental costs and inefficient use of valuable diagnostic resources.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in accordance with some embodiments of the present invention, a device for facilitating tissue sampling using Fine Needle Aspiration (FNA). At a distal end of the device, multiple needles are extendible, and are disposed such that a first central needle is surrounded by a plurality of second outer needles.

In some embodiments, the first needle is advanced through and out of the device separately and independently from the plurality of second needles. Typically, the first needle is advanced first into the tissue, to facilitated anchoring of the device in the tissue. Subsequently, the plurality of second needles is advanced out of the device to contact and engage the tissue. In some embodiments, the plurality of second needles that surround the first needle is disposed in a staggered arrangement such that a portion of those needles contacts and engages the tissue prior to another portion of those needles. As a result, the outer needle that first engages the sampled tissue, is configured to pierce the tissue with little or no resistance, enabling both tissue collection by the needle, as well as, subsequent engagement of the tissue by the following outer needle.

In some embodiments, the first central needle is shaped to define a side-facing port to facilitate anchoring of the needle in the tissue to be sampled. Typically, the side-facing port is in communication with the lumen of the needle and has a proximally facing distal edge. Typically, when engaging the tissue, a portion of the tissue is drawn into the port such that the needle is constraint from proximal motion due to the distal edge of the port contacting the tissue drawn into the port (the tissue acting as a stop for the needle when the distal edge is brought against the tissue in the port, thereby inhibiting unintentional slippage of the needle in a proximal direction, out of the tissue). When the operating physician is prepared to withdraw the needle from the tissue, a force which exceeds a predetermined threshold is applied by the physician in order to pull the needle proximally and remove it from the tissue.

In some embodiments, in additional to independent movement of the needles, the device is configured to independently apply suction to the first needle and the plurality of other needles surrounding the first needle (e.g., via a separate port).

In some embodiments, the device is configured to adjust a surface area of the tissue that is engaged by the tissue sampling device by controlling an extent to which the multiple needles spread outwardly with respect to a central longitudinal axis of the device, thereby adjusting the device for use with target tissues of varying sizes and shapes.

Three is thus provided, in an embodiment, an apparatus for sampling a biopsy target, the apparatus comprising: a sheath, shaped to define a plurality of openings at a distal end of the sheath; an elongate first needle extendible perpendicularly from a distal end of said sheath through one of said plurality of openings; and an assembly comprising at least two second needles arranged in a predetermined pattern relative to said first needle, and extendible perpendicularly from said distal end of said sheath, wherein each of said second needles is extendible out of one of said plurality of openings, wherein, when extended from said distal end of said sheath: (i) each of said second needles extends a different length from said distal end of said sheath, (ii) at least a distal portion of each of said second needles is resiliently biased to extend laterally outwardly in relation to said first needle, and (iii) a lateral spread region defined by said distal portions of all of said second needles is determined based, at least in part, on a distance of said extending from said distal end of said sheath.

There is also provided, in an embodiment, a method for sampling a biopsy target, comprising: providing an apparatus comprising a sheath, shaped to define a plurality of openings at a distal end of the sheath, an elongate first needle extendible perpendicularly from a distal end of said sheath through one of said plurality of openings, and an assembly comprising at least two second needles arranged in a predetermined pattern relative to said first needle, and extendible perpendicularly from said distal end of said sheath, wherein each of said second needles is extendible out of one of said plurality of openings, wherein, when extended from said distal end of said sheath: (i) each of said second needles extends a different length from said distal end of said sheath, (ii) at least a distal portion of each of said second needles is resiliently biased to extend laterally outwardly in relation to said first needle, and (iii) a lateral spread region defined by said distal portions of all of said second needles is determined based, at least in part, on a distance of said extending from said distal end of said sheath; extending said first needle to engage said target side; and extending said assembly to engage said target side.

In some embodiments, the first needle and said assembly are each configured to be extendible independently of one another.

In some embodiments, the first needle comprises at least one anchoring element configured to prevent a migration of said apparatus from said biopsy target, wherein said at least one anchoring element is selected from the group consisting of: an inflatable element, a suction element, a gripping element, a retractable spike, a serration, a threaded portion, a crossbar element, and a side-facing aperture.

In some embodiments, the anchoring element is a side-facing aperture at a distal portion of said first needle, wherein said said-facing aperture is configured to receive a portion of said biopsy target therein, and wherein said side-facing aperture comprises a distal edge configured to incise said biopsy target only upon application of a predetermined amount of axial force.

In some embodiments, the predetermined pattern comprises said at least two second needles arranged in a surrounding pattern relative to said first needle.

In some embodiments, the apparatus further comprises a manipulating hub coupled to said sheath, wherein said manipulating hub comprises a first and second slide members configured to reciprocally slide distally and proximally along a common axis.

In some embodiments, the said reciprocal sliding of said first slide member is configured to reciprocally extend and retract said first needle from said distal end of said sheath; and said reciprocal sliding of said second slide member is configured to reciprocally extend and retract said assembly from said distal end of said sheath.

In some embodiments, an extent of said reciprocal sliding of said second slide member in the distal direction is determined by an axial position of said first slide member.

In some embodiments, the reciprocal sliding of said second slide member in the distal direction is only possible following said reciprocal sliding of said first slide member in the distal direction.

In some embodiments, the manipulating hub comprises a stop located distally to said first slide member, wherein said stop determines a maximal said reciprocal sliding of said first slide member in the distal direction.

In some embodiments, at least a portion of said manipulating hub is selectively rotatable (i) in tandem with or (ii) relative to said sheath.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 9A-9C are schematic illustrations of a first central needle for use with the device, in accordance with some embodiments of the present invention.

DETAILED DESCRIPTION OF THE INVENTION

Some embodiments of the present invention provide a tissue sampling device for facilitating accurate, reliable and safe sampling of a biopsy target tissue. Typically, the device is configured to sample multiple locations and/or multiple depths of the biopsy target tissue during a single sampling procedure, while anchoring the device in the biopsy target tissue to reduce the risk of displacement of the device during the sampling procedure.

In some embodiments, the present device is configured for obtaining multiple samples associated with multiple locations within a sampled tissue, by operating a plurality of sampling needles extendible from a distal end of the device.

In some embodiments, at a distal end of the device, multiple needles are extendible, and are disposed such that a first central needle is surrounded by two or more outer needles. Typically, the first central needle is advanced into the target tissue first, to engage the target tissue and provide anchoring of the device in the target tissue. After anchoring the central needle in the tissue, the surrounding outer needles are advanced and extended to engage the tissue at a plurality of respective locations surrounding the central needle. In some embodiments, the plurality of outer needles may be advanced individually or as a group. In some embodiments, the plurality of outer needles may be configured to engage the tissue at a staggered or sequential fashion, e.g., one at a time.

At a proximal end of the device, a needle control housing is disposed to allow manual control of the extendable needles. For example, the tissue sampling device is configured to independently control extension of the first central needle and extension of the outer second needles (either individually or as a group). In accordance with some embodiments of the present invention, independent control over the two needle groups (central and outer) is achieved through a single handle (as opposed to two separate handles for separately controlling each group of needles).

Figure 1:
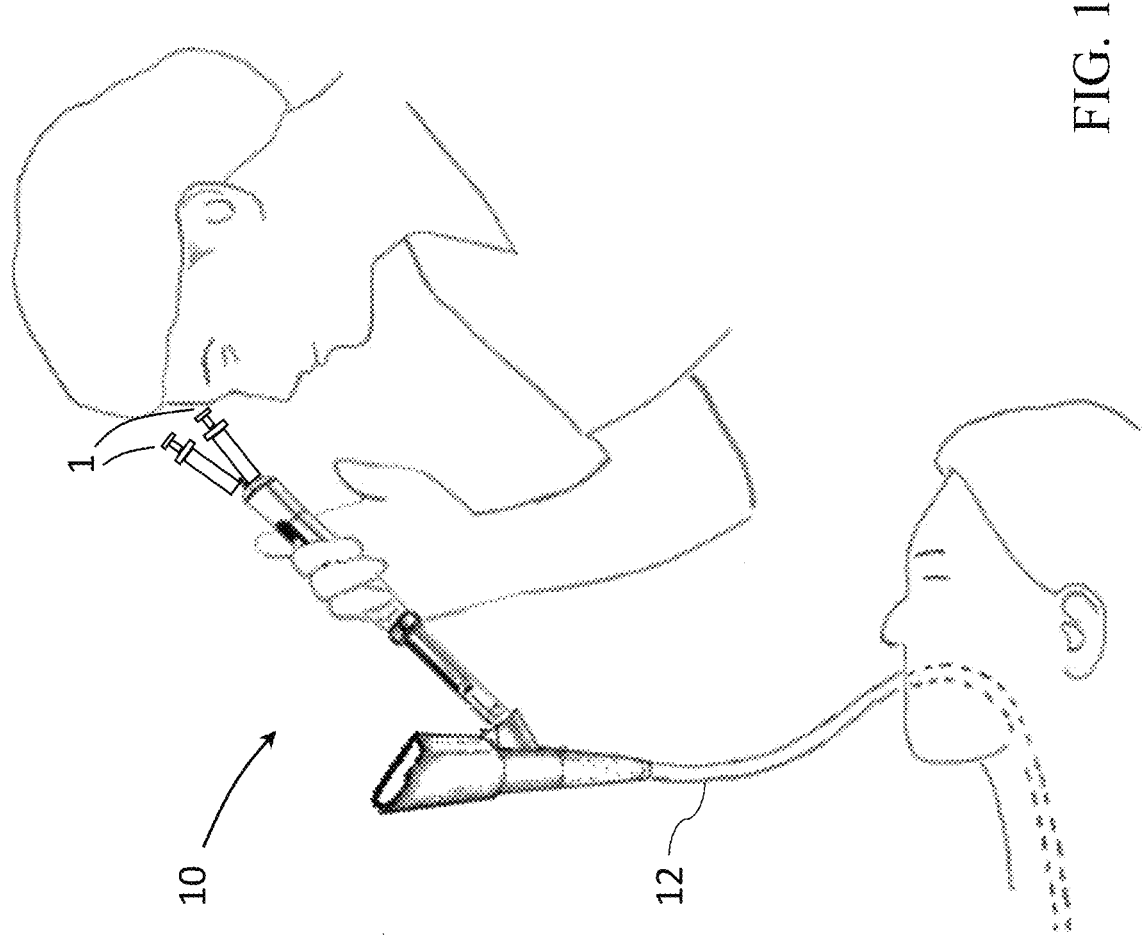
FIG. 1 is a schematic illustration of a tissue sampling device and a guiding tool, in accordance with some embodiments of the present invention.

Reference is first made to FIG. 1, which is a schematic illustration of a device 10, in accordance with some embodiments of the present invention. Device 10 is used for obtaining one or more tissue samples (e.g., biopsy samples) in a fine-needle aspiration biopsy (FNAB) procedure, and is typically advanced through a guiding tool 12 (such as an ultrasonic endoscope) in an FNA procedure such as an EUS-FNA procedure. FIG. 1 is a view of device 10 being used with a guiding tool 12, such as an endoscope, e.g., an ultrasonic endoscope. Device 10 is typically used with such a guiding tool but may alternatively be used without such a guiding tool (e.g., by being manually guided). In FIG. 1, a physician is shown using device 10 with the assistance of guiding tool 12 for navigation through a natural orifice of a patient, in this case a mouth of the patient in order to reach tissue targeted for sampling. For example, guiding tool 12 may be used to guide and navigate device 10, e.g., past the esophagus toward target internal organs where diagnostics may be required, such as towards the pancreas. Device 10 is shown comprising two syringes 1 at a proximal end of a needle control housing, arranged to apply suction for assisting in obtaining samples from a patient being diagnosed. It is noted that although not shown in all figures, these syringes, or any other suction element, may be suitably fixed at the proximal end of device 10 during operation in fluid communication with internal lumens of the needles for application of suction through the needles.

In this context, in the specification and in the claims, "proximal" means closer to the orifice through which the sheath is originally placed into the body, and "distal" means further from this orifice.

Figure 2:
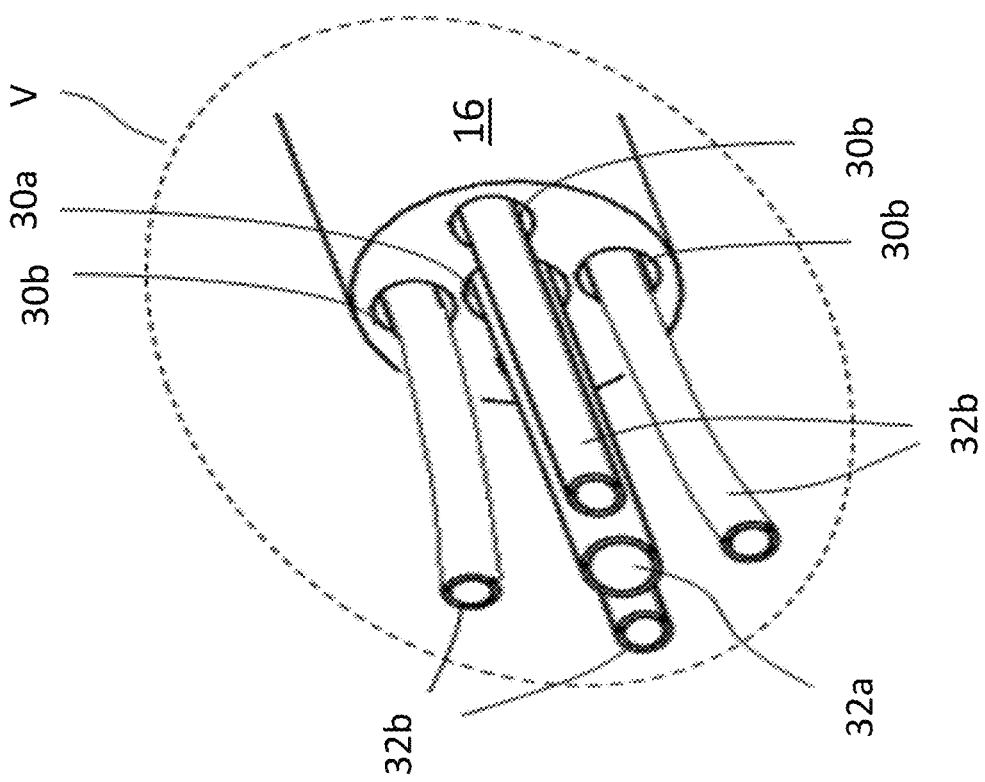
FIG. 2 is a schematic illustration of the tissue sampling device, in accordance with some embodiments of the present invention.

Reference is now made to FIG. 2, which is a schematic illustration of distal portion of device 10, in accordance with some embodiments of the present invention. A distal portion of device 10 comprises a distal end of sheath 16, which terminates at a needle-control housing (not shown) at a proximal portion of device 10.

Typically, sheath 16 is flexible, and is shaped to be advanced through a working channel of guiding tool 12 in FIG. 1. For example, guiding tool 12 may be a steerable ultrasonic endoscope, and sheath 16 may be advanceable through a working channel of the endoscope. For example, tool 12 and device 10 may be advanced into the gastrointestinal tract and used to obtain a sample of a tissue of the gastrointestinal tract, or tissue proximal to the gastrointestinal tract. Alternatively, sheath 16 may be rigid, and/or tool 12 may be a rigid trocar. For some applications, sheath 16 may be used without tool 12.

Sheath 16 may be arranged to house multiple inner needles, optionally each including an inner stylet, to inhibit entry of tissue into the internal lumen of each needle until after the stylets are removed by pulling them proximally.

Sheath 16 defines a plurality of openings 30 at a distal end thereof (the distal end of sheath 16 indicated as section V marked within a dashed ellipse in FIG. 2). The plurality of openings 30 comprises a first opening 30a, and a plurality of second openings 30b surrounding opening 30a. It is to be noted that, in this context, the term "surrounding" (including the specification and the claims) means that if one were to draw polygon enclosing all of openings 30b, opening 30a would generally be disposed near a geometric center of such polygon. However, for some embodiments, opening 30a may be disposed elsewhere within the polygon, on an edge of the resulting polygon, or outside of the polygon. The multiple needles that are housed in sheath 16 extend through openings 30 to engage the target tissue during operation of device 10.

Figure 3A:
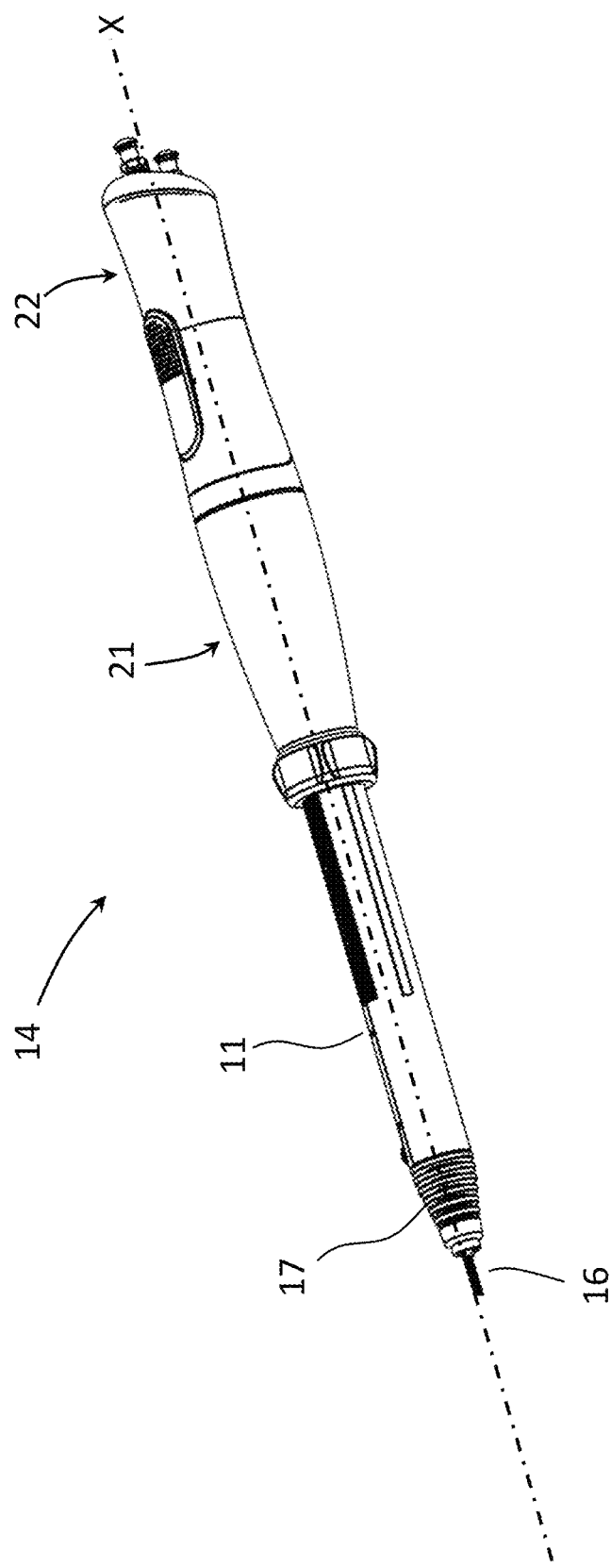
FIGS. 3A and 3B are schematic illustrations of the tissue sampling device, in accordance with some embodiments of the present invention.
Figure 3B:
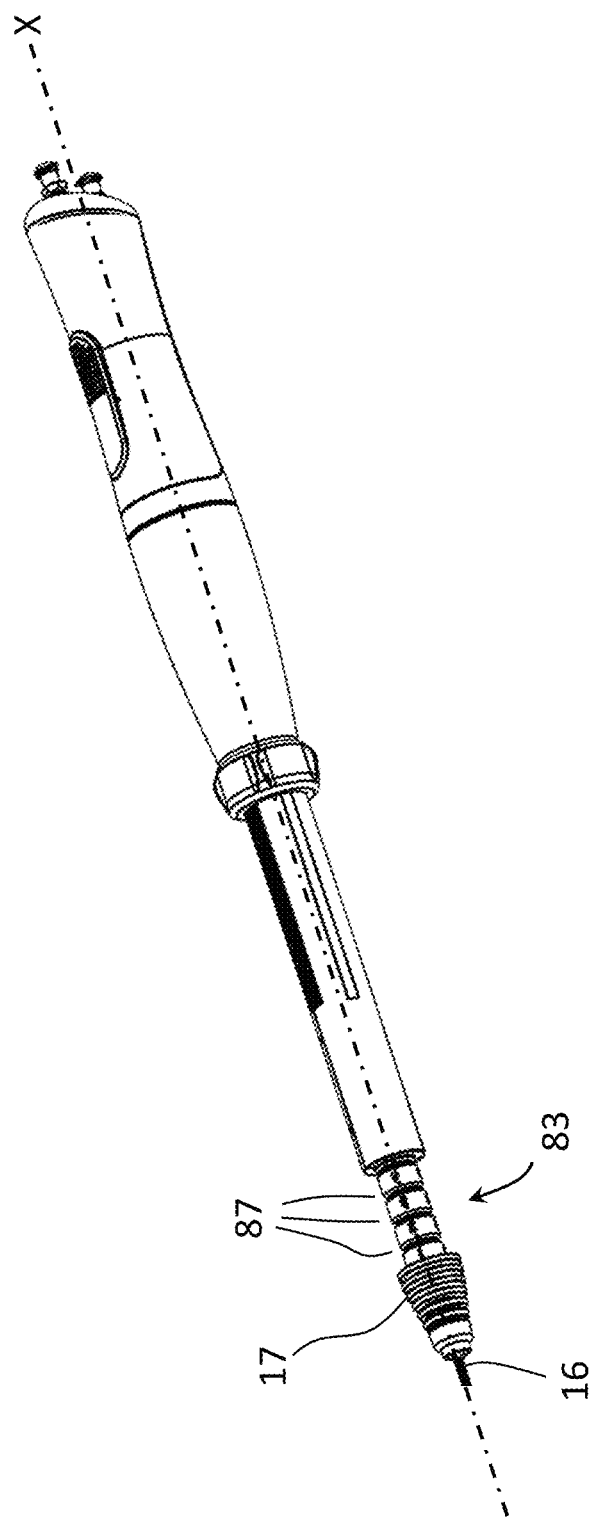

Reference is now made FIGS. 3A-B, which are a closer view of needle-control housing 14 coupled to the proximal portion of sheath 16. In FIG. 3A, housing 14 is shown comprising a main shaft 11 and a first and second slide needle control slide members 21, 22 that are configured to slide axially generally along an axis X defined by shaft 11.

In some embodiments, device 10 comprises an adapter 17 disposed at a distal portion of shaft 11. Adapter 17 is used to configure device 10 for use with guide tools 12 (e.g. endoscopes) of varying lengths by adjusting an effective length of sheath 16.

Adapter 17 is configured to slide axially with respect to shaft 11 in the distal or proximal directions over sheath 16 (i.e. while the sheath remains substantially fixed in place) and by that shorten or lengthen, respectively, the length that sheath 16 extends away from the from adapter 17. Urging adapter 17 in the distal direction over and relative to sheath 16 (as in FIG. 3B) causes the length of the sheath extending beyond the adapter to shorten; and urging adapter 17 in the proximal direction over and relative to sheath 16 (as in FIG. 3A)—causes the length of the sheath extending beyond the adapter to increase.

In some embodiments, device 10 is lockable to endoscope 12, e.g., via a Luer-type lock fitting that mates with a counterpart fitting on the endoscope. Typically, this fitting is coupled to (or defined by) offset adapter 17. Typically, a distal end of adapter 17 (shown by example to be generally cone shaped) may be arranged to fit the Luer-lock of the endoscope while sheath 16 extends through the lumen of the endoscope towards the target tissue within the body of the patient. Adapter 17 may be fitted with markings for assisting in adapting device 10 to different endoscopes, and once a desired relative position of the adapter has been reached it may be fixed in place using a fastener 2 (see shown in FIGS. 5 and 7).

A fastener of device 10 (not shown) may take various forms, such as a screw, a spring-loaded pin (pogo pin), or the like. In its spring-loaded pin formation, the fastener may be arranged to snap into peripheral slits 87 formed about a stem 83 of the adapter that may be substantially revealed as the adapter is distally urged away from shaft 11. Such slits 87 may also form indications of pre-set distances that the adapter can be set at—that may fit pre-defined endoscope types that device 10 may be set to work with.

Reference is still made to FIGS. 2 and 3A-B. As noted hereinabove, needle-control housing 14 comprises first and second control slide members 21, 22, respectively. Typically, first control slide member 21 is disposed co-axially and distally to second control slide member 22. Control slide member 21 is attached to a first elongate needle 32a, such that sliding of slide member 21 with respect to housing 14 (along axis X) slides needle 32a through sheath 16, such that a distal tip of the needle moves with respect to opening 30a (e.g., the tip moves through the opening, such as out of the opening). Control slide member 21 is attached to a plurality of second elongate needles 32b, such that sliding of slide member 21 with respect to housing 14 (along axis X) slides needles 32b through sheath 16, such that a distal tip of each needle 32b moves with respect to a respective opening 30b (e.g., the tip moves through the respective opening, such as out of the respective opening).

Although needle 32a is described and shown as being a single needle, for some applications needle 32a is a plurality of needles, mutatis mutandis. Additionally, or alternatively, the number of second needles 32b may vary from the example of four needles shown in FIG. 2, to any other suitable number of needles, e.g., such as in a device suited for sampling the prostate more than four needles 32*b* may be used (e.g. 2, 3, 4, 5, 6, or more needles 32*b*).

Figure 4:
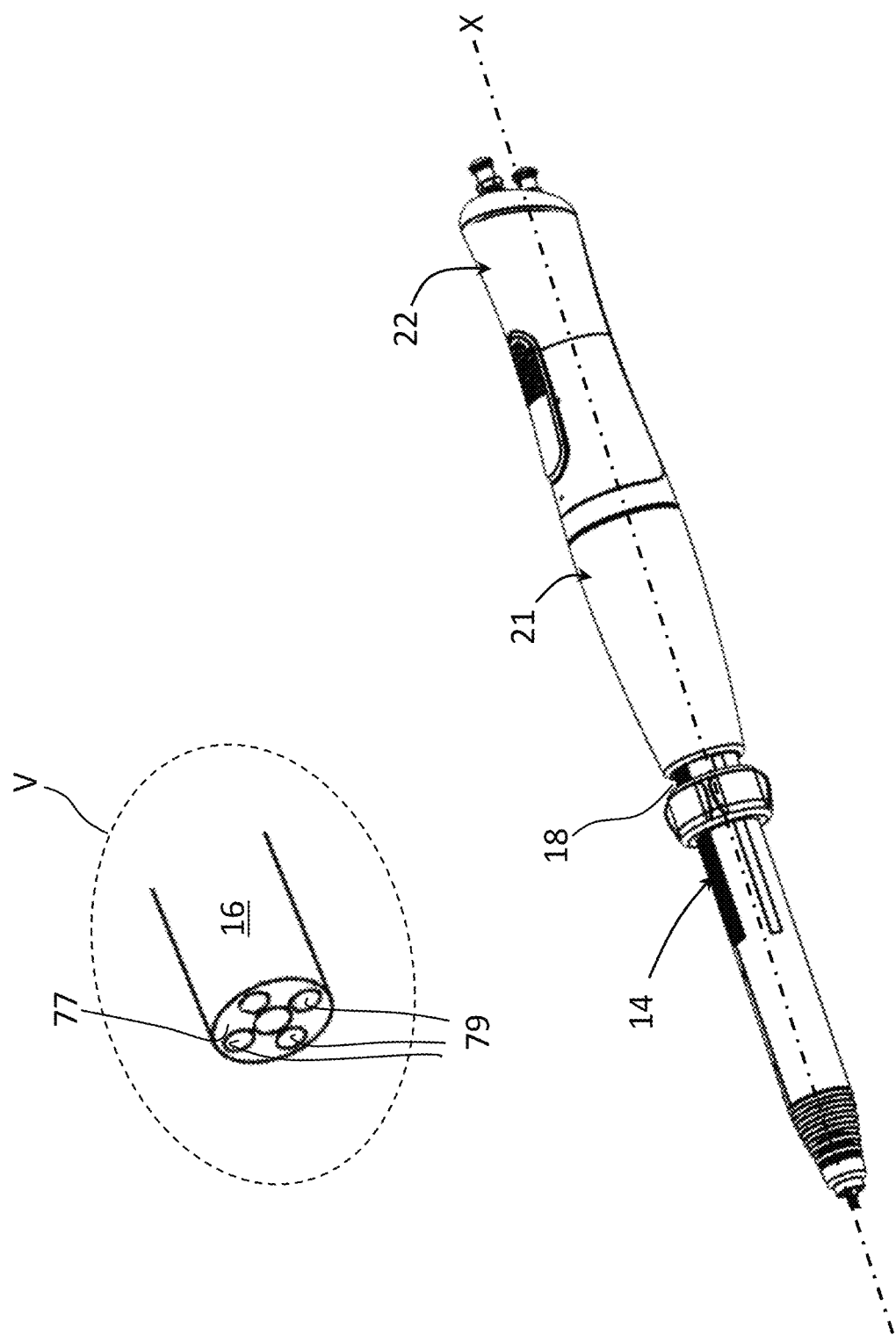
FIG. 4 is a schematic illustration of the tissue sampling device, in accordance with some embodiments of the present invention.
Figure 5:
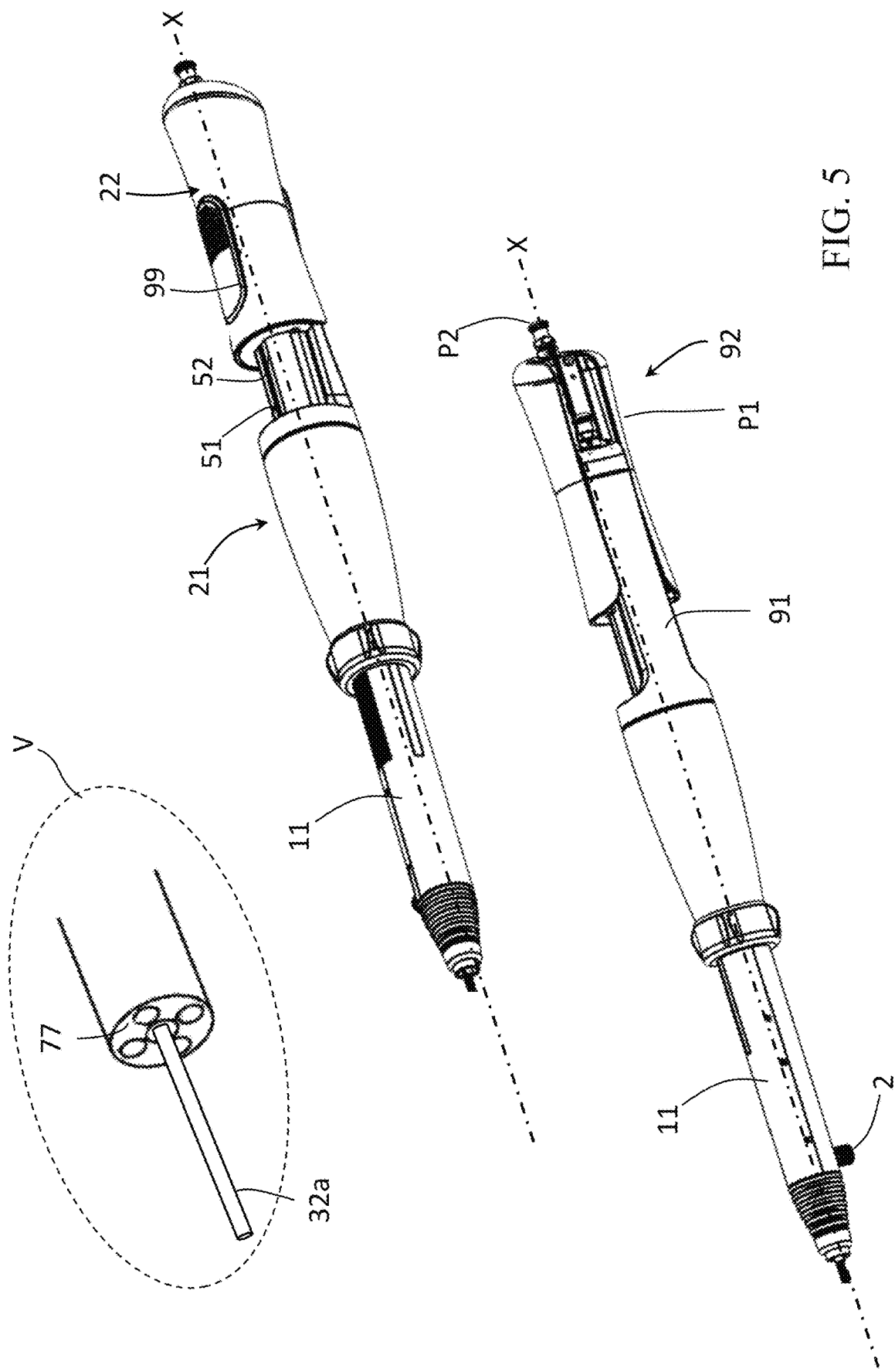
FIGS. 5 and 6 are schematic illustrations showing use of the device in respective states thereof, in accordance with some embodiments of the present invention.

Reference is now made to FIGS. 4-5, which are schematic illustrations of device 10 being operated with a stopper 18, in accordance with some embodiments of the present invention. In some embodiments, (e.g., subsequently to adapting device 10 to different endoscope lengths), stopper 18 is used to stop the movement of slide members 21 and 22 and hence the needles may be maneuvered along shaft 11 to define a distal extent that the first and second slide members 21, 22 (and their respective needles 32*a* and 32*b*) may extend distally beyond the distal tip 77 of sheath 16. In FIG. 4, slide members 21, 22 have yet to be advanced distally and thus no needles extend beyond tip 77. Additionally, in FIG. 4 it is shown that each needle may be arranged to have a distinct channel 79 through which it may pass through openings 30 and sheath 16.

FIG. 5 illustrates a first operative step of advancing first slide member 21 in the distal direction towards stopper 18. Distal advancement of slide member 21 causes central main needle 32*a* to extend beyond tip 77 of sheath 16. Subsequently to first slide member 21 being advanced distally along shaft 11, the generally collinear arranged second slide member 22 is free to trail along the same axial route and advance distally along shaft 11 in order to urge the plurality of second needles 32*b* to extend beyond tip 77 and out of sheath 16. In some embodiments, all, or a portion of, the plurality of second needles 32*b* may be arranged to not extend beyond the extension of first needle 32*a*. It is thus noted that the first slide member 21 in the shown embodiments may be arranged to function as a stop for second slide member 22. For example, an operator of the present system may first advance slide member 21 a first desired axial distance, which may result in first needle 32*a* extending a corresponding first distance beyond tip 77. Subsequently, the operator may advance slide member 22 a second desired axial distance, which may not exceed the first desired axial distance and which may result in the plurality of second needles 32*b* extending beyond tip 77 a corresponding second distance which may not exceed the first corresponding distance.

In some embodiments, first slide member 21 comprises a proximally-facing bumper 51 and second slide member 22 comprises a distally-facing bumper 52, such that advancing second slide member 22 distally along shaft 11 is possible only until bumper 52 meets bumper 51. In the illustrated example, first slide member 21 may be seen including an extension 91 at its rear side that extends in a rear proximal direction beyond rear facing bumper 51 generally along-side axis X.

Such sliding movement along axis X typically ensures that first slide member 21 with its needle 32*a* moves first into a sample to be diagnosed thus forming a so-called anchor within the sample. And after first slide member 21 advanced distally, making space for the distal advancement of second slide member 22, the second slide member 22 can be manipulated to move distally together with second needles 32*a* into the target tissue.

Second slide member 22 includes an elongated recess 92 for receiving extension 91 as the first slide member 21 slides distally and proximally along axis X. Extension 91 houses at its rear side a port P1 where communication between a syringe and the main central needle 32*a* controlled by slide member 21 can be obtained. A second port P2 for communicating between a syringe and the secondary needles 32 can be seen located at a rear end of the second slide member 22.

Figure 6:
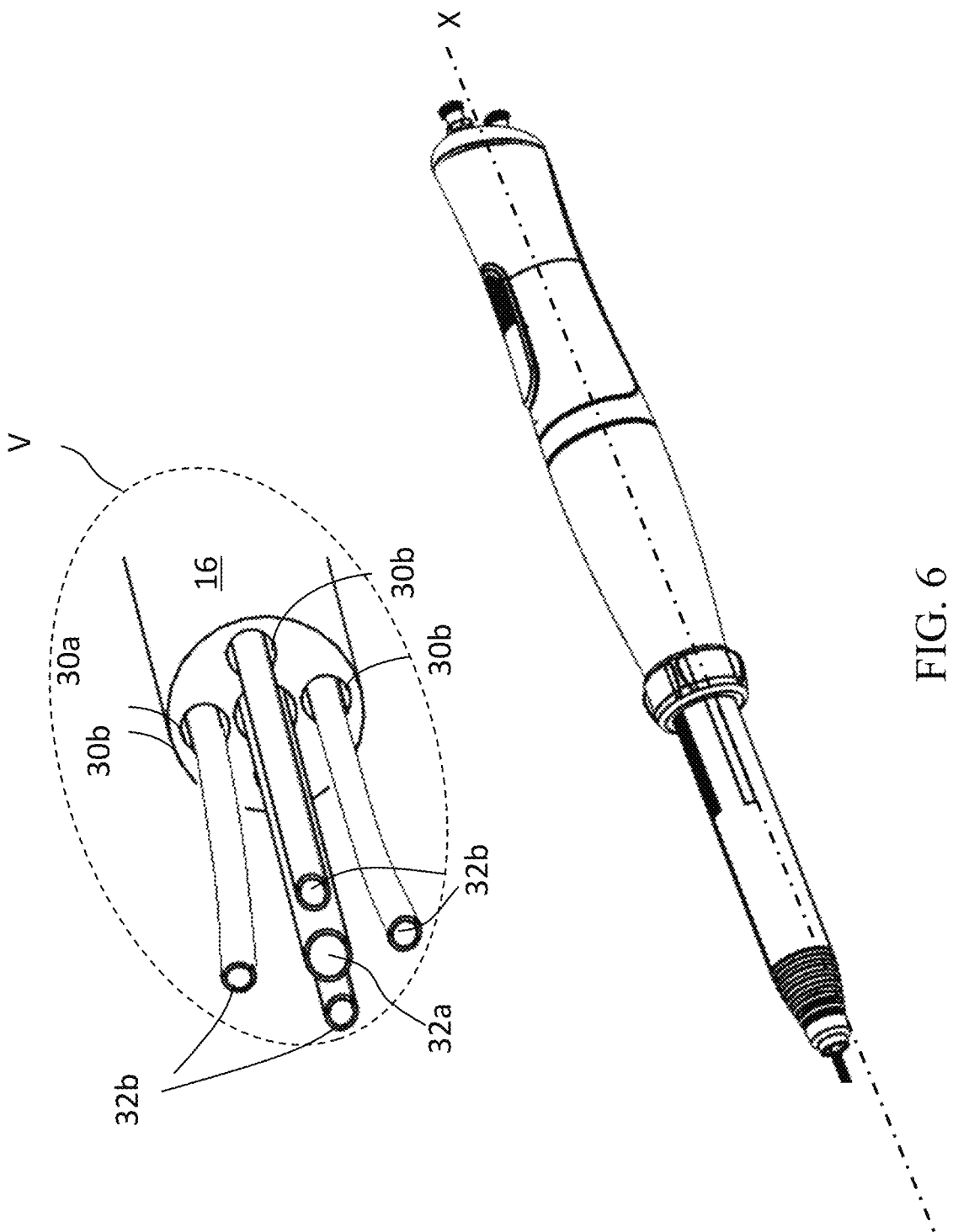

In some embodiments, second slide member 22 is advanced distally until it accordingly meets and abuts against bumper 51 of the first slide member 21. As a safety measure, second slide member 22 may be fitted with a toggle 99 and may be inhibited from starting to move in the distal direction until toggle 99 is manually manipulated (e.g. by pressing the toggle). Such movement of second slide member 22 possibly after toggle 99 has been pressed can be seen in FIG. 6.

In an aspect of the present invention, needle control housing 14 may be arranged for manipulation by a physician with minimal complexity. For example, in the illustrated example, it is envisioned that a physician may manipulate device 10 at needle control housing 14 using a single hand. By arranging needle control housing 14 to include two members 21, 22 that are disposed to coaxially slide one trailing the other along a common axis X, ease of use with substantially a single hand is facilitated.

In embodiments, toggle 99 provides an additional safety measure making device 10 substantially error-proof by requiring positive feedback from a possibly preoccupied physician handling the procedure—that he/she indeed intends to advance the secondary needles 32 into the sample to be diagnosed.

Figure 7A:
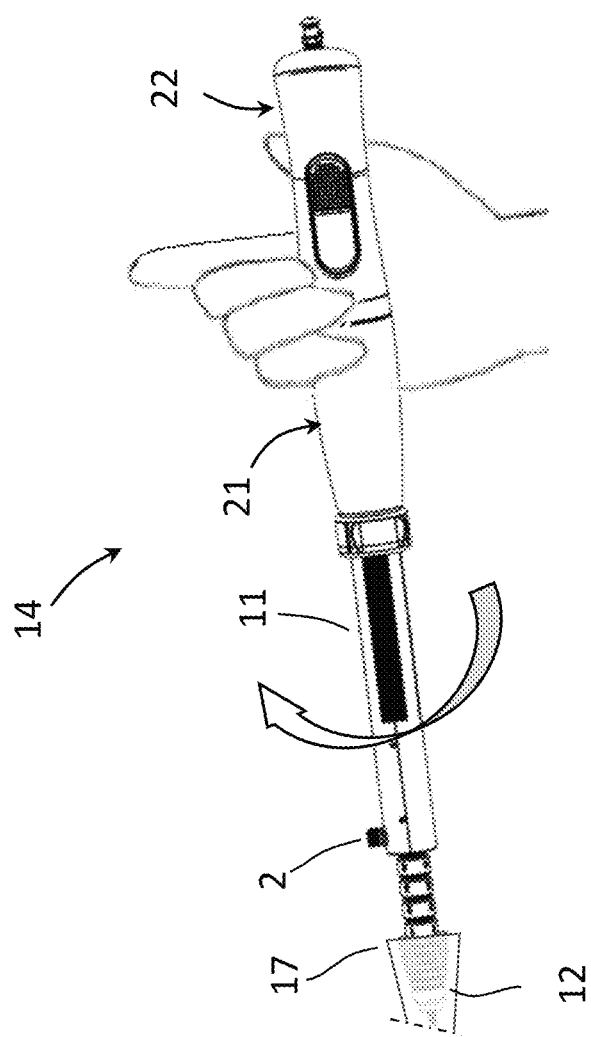
FIGS. 7A and 7B are schematic illustrations of the tissue sampling device suitable for rotation relative to an adapter thereof.
Figure 7B:
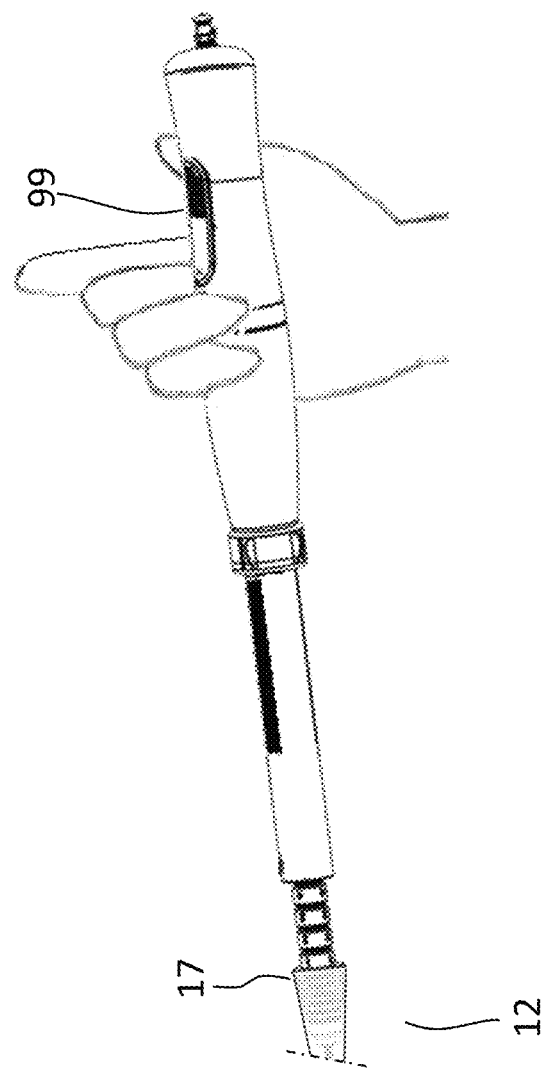

Reference is now made to FIGS. 7A and 7B illustrating an aspect of the present invention. In certain embodiments, the shaft 11 together with sliding members 21, 22 may be adjusted to rotate relative to adapter 17, while device 10 is being used in a diagnostic procedure. Adapter 17 during such diagnostic procedures may accordingly be "parked" at a Luer-lock of an endoscope 12, and rotation of the shaft 11 and sliding members 21, 22 may be relative to the adapter that is maintained substantially fixed in place at the Luer-lock.

Such rotation of the sliding members may be utilized in certain cases while both the main (first needle 32*a*) and second needles (plurality of needles 32*b*) are extended into the target tissue in a procedure that may assist in obtaining larger samples from a diagnosed tissue due to the shear action of the needles as they cut/dig into the diagnosed sample during rotation of housing 14.

In certain cases, such rotation may be used to sample different locations in a target tissue, while in between sampling, needles may be retreated away from the tissue before being advanced back into the tissue at a new rotated location. For example, a first sampling of a target tissue may be performed while both the main and secondary needles penetrate the tissue to obtain samples, and then while the main needle 32*a* remains placed within the sample (acting as a so-called 'pivot') the second needles 32*b* may be retreated and then needle control housing 14 (excluding the adapter) may be rotated to position second needles 32*b* above a new location in the tissue that may then be sampled by sliding the second sliding member 22 forward.

In certain cases, housing 14 may be configured for allowing 'free-wheel' rotation of housing 14 relative to endoscope, to allow repositioning housing 14 for convenient access to the features of housing 14 for the operator. For example, housing 14 may be so rotated to position toggle 99 in a position more convenient for activation by a physician during a diagnostic procedure. Toggle 99 may be here seen re-positioned from the orientation seen in FIG. 7A that may be less convenient for physician—to the position seen in FIG. 7B that may be more convenient for the physician for activation of the toggle by one of his/her fingers.

Such 'free-wheel' rotation during a biopsy procedure of housing 14 with respect to adapter 17 (that is locked with the endoscope's Luer-lock), may be performed while the adapter maintains its pre-set axial calibration relative to shaft 11. This is typically accomplished by utilizing a fastener with a spring-loaded pin formation that remains pressed in a peripheral slit 87 of the adapter (thus maintaining the pre-defined axial calibration). Manual rotation of the housing 14 relative to the adapter may then be performed while fastener 2 together with shaft 11 (and remaining parts of the housing 14) is urged to rotate along the peripheral slit where it is located.

Reference is now made to FIGS. 8A-8D, which are schematic illustrations of an exploded view of multiple FNA and/or FNB needles extending beyond the distal end of device 10, in accordance with some embodiments if the present invention. Embodiments of device 10 may be arranged to perform various diagnostic procedures such as FNA, FNB (or the like), and thus, may be fitted with suitable needle sets for such procedures or combination of procedures. Generally, FNA and FNB needles are known in the art. These are fine hollow needle with a sharpened piercing tip (e.g., 19 gauge or smaller, and typically 22-25 gauge), used to obtain a sample from a tissue.

In some embodiments, device 10 may include a combination of a first group of one or more FNB needles and second group of FNA needles or vice-versa. Alternatively, the first group can have one diameter needles (e.g. 22 gauge or the like) while the second group can have different diameter needles than the first group (e.g. 25 gauge or the like).

In some embodiments, as shown in FIGS. 8A-8D, device 10 comprises a needle arrangement in which a first central needle 32a is surrounded by a plurality of second outer needles 32b. First central needle 32a is in fluid communication with a first one of syringes 1 (shown in FIG. 1), while typically all second outer needles 32b are in fluid communication with a single other one of syringes 1.

Typically, needles 32a and 32b are long (e.g., ranging in length between 100-200) and flexible. For some applications, needles 32b are of higher gauge than is needle 32a, or needle 32a may be of a higher gauge of needles 32b.

Figure 8A:
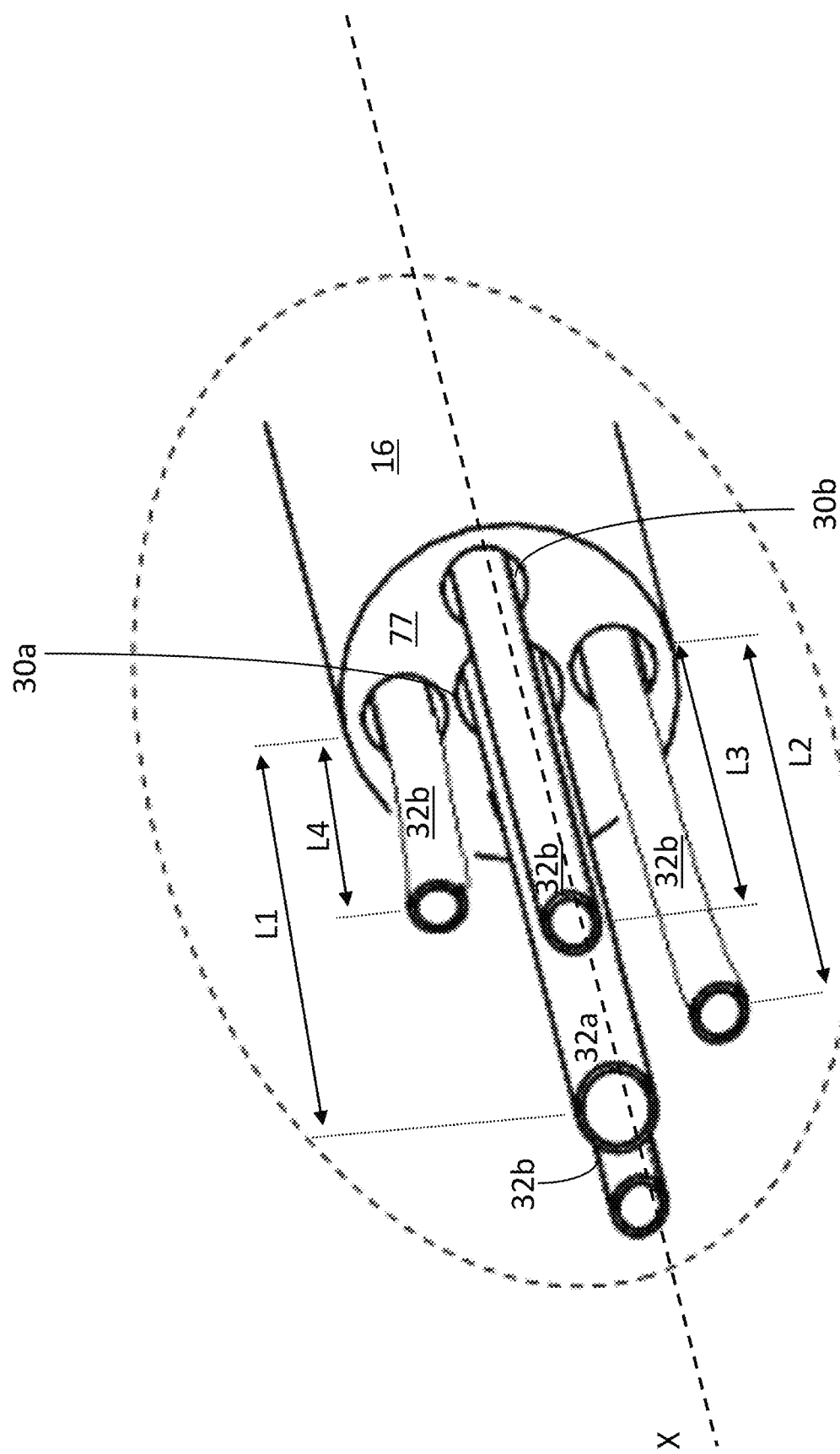
FIGS. 8A-8D are schematic illustrations of the distal portion of the device, in accordance with some applications of the invention.
Figure 8B:
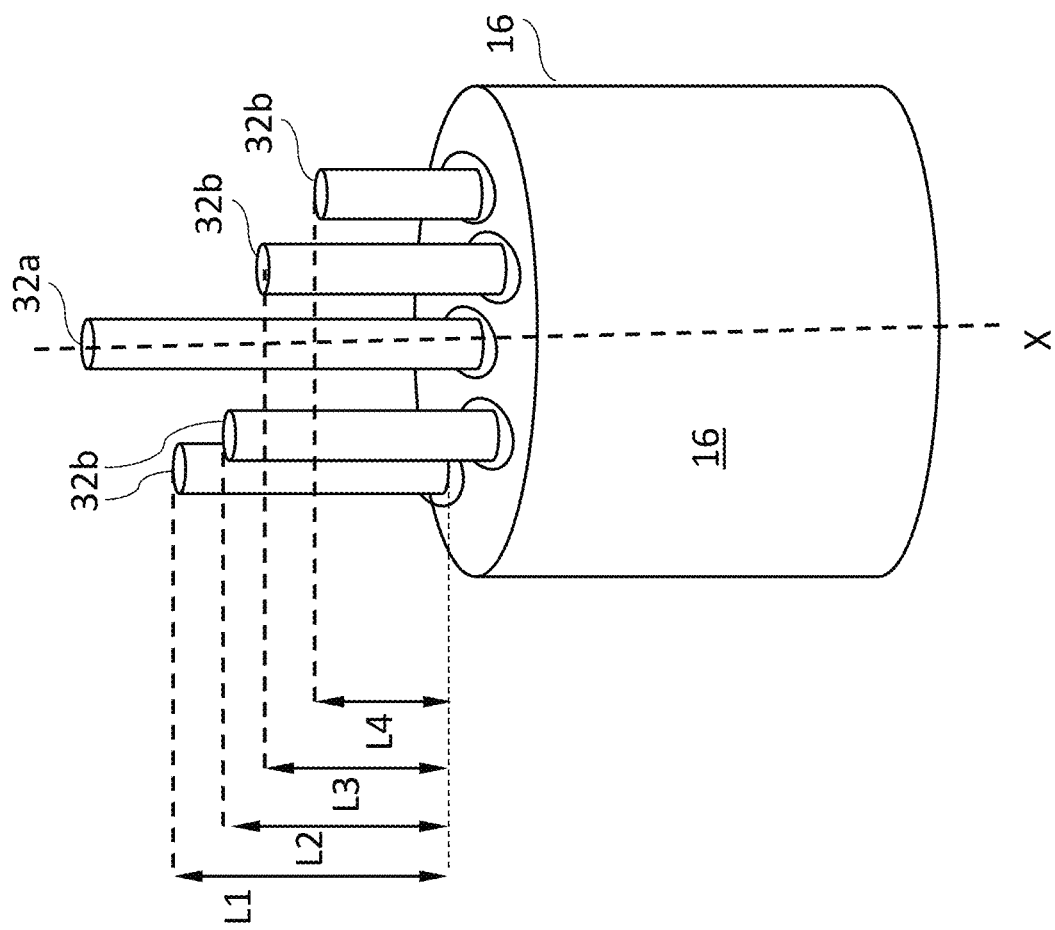

Reference is made to FIGS. 8A-8B. Typically, during operation, first needle 32a is advanced first into the tissue to be sampled, in order to facilitated anchoring of device 10 in the tissue. Subsequently, outer needles 32b are advanced as a group to be extended out from sheath 16 into the target tissue. As shown, in some embodiments, outer needles 32b surrounding first needle 32a extend distally in a staggered configuration, where, when advances in unison, needles 32b are configured to engage the tissue in sequence, e.g., one after another.

Accordingly, during a tissue sampling procedure, the tip of one of the outer needles 32b is configured to contact and engage the tissue to be sampled prior to another outer needle. As a result, during advancement of the needles, the sampled tissue is being engaged by only one needle at a time, to facilitate penetrating the tissue with little or no resistance and with little or no displacement of the tissue surface to be penetrated. Thus, all needles 32a and 32b may be configured to engage the sampled tissue sequentially, so as to minimize the possibility of tissue displacement as a result of multiple simultaneous engagements by multiple needles. Typically, use of multiple staggered needles maximizes the amount of tissue to be harvested in a controlled manner while reducing the risk of tissue displacement.

In some embodiments, as shown in FIGS. 8A-8B, staggered needle engagement may be facilitated by having needles 32b be of varying lengths extending beyond a distal tip 77 of sheath 16 in respective extended states suitable for obtaining tissue samples. A first needle 32b may be seen having a generally similar length L1, with each one of the remaining outer surrounding needles 32b having respective lengths L2, L3, L4. The lengths L2 to L4 may be smaller than L1 and in one example each one of these lengths may be different. As noted hereinabove, provision of such different lengths of outer needles 32b may assist in some cases in ensuring suitable needle penetration into a body organ for obtain tissue sample. In one possible generalization each needle may be arranged to have a length $L_x$, to ensure staggered gradual needle penetration, and the number of needles having the same $L_x$ can change, and/or each needle can have a different length, optionally each two have the same length, etc. Each needle 32b is hypothesized to reach a different part of the tissue from that reached by the other needles 32b, and from that reached by needle 32a.

In some embodiments, needles 32a and 32b (or at least a distal portion thereof) may be biased to be straight. That is, in the absence of an external force, the distal portion of needles 32a and 32b are typically straight. Therefore, when disposed outside of openings 30a and 30b, the distal portion of needles 32a and 32b typically extends perpendicularly to a distal face of sheath 16.

Alternatively, some or all of needles 32b (or at least a distal portion thereof) may be resiliently biased such that at least an exposed distal portion thereof extends laterally and/or radially outwardly relative to needle 32a and/or a central axis X of sheath 16. That is, in the absence of an external force, when extended outside of opening 30b, at least a portion of an exposed distal portion of at least some of needles 32b resiliently extends laterally and/or radially outwardly in relation to needle 32a and/or in relation to a central axis X of sheath 16.

Optionally or additionally, some or all of needles 32b (or at least a distal portion thereof) may be formed with a specified curvature which results in at least an exposed distal portion of needles 32b extending laterally and/or radially outwardly relative to needle 32a and/or a central axis X of sheath 16. That is, in the absence of an external force, when extended outside of opening 30b, at least a portion of an exposed distal portion of at least some of needles 32b tend to curve laterally and/or radially outwardly in relation to needle 32a and/or in relation to a central axis X of sheath 16.

In some embodiments, needles 32b are arranged such that when exposed from the distal end of sheath 16, needles 32b diverge and/or spread outwardly relative to first central needle 32a. In some embodiments, this may result in at least some of needles 32b entering the tissue at a non-perpendicular angle to a surface of the tissue, e.g., at a non-90 degree angle relative to a surface of the tissue.

Figure 8D:
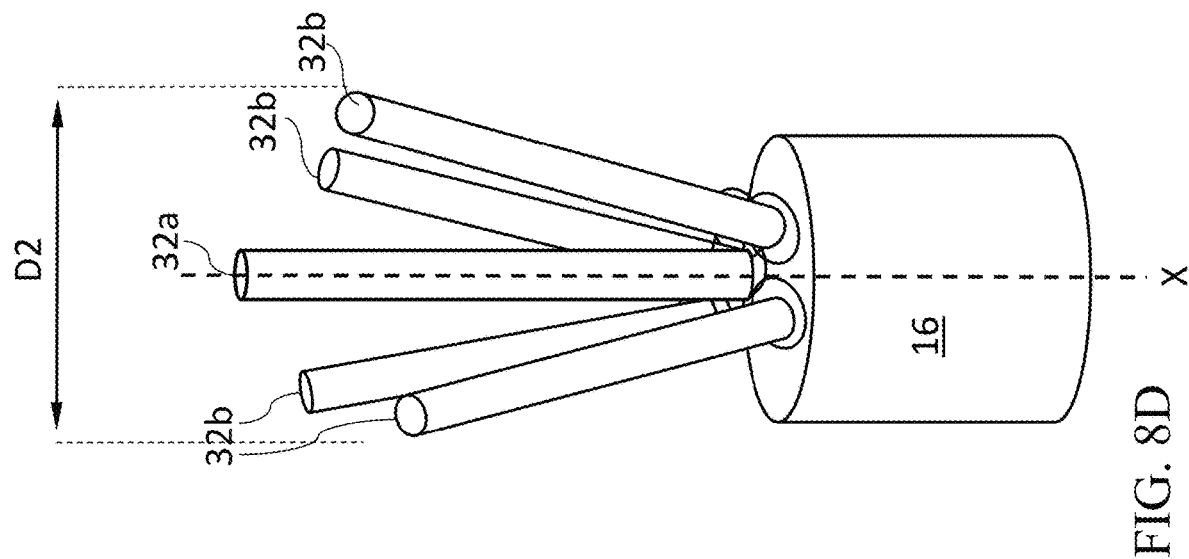
Figure 8C:
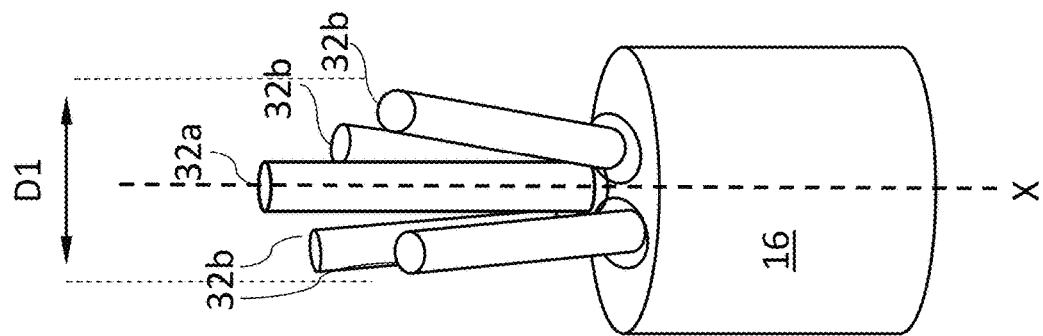

In some embodiments, a lateral spread of distal tips of needles 32b may be controlled based, at least in part, on the extent to which needles 32a are extended out of sheath 16. Accordingly, as can be seen in FIGS. 8C-8D, the greater the extent to which needles 32b are extended from a distal face of sheath 16, the greater the lateral spread or span D1, D2 of distal tips of needles 32b.

In some embodiments, a lateral spread or span, e.g., D1, D2, of distal tips of needles 32b may be adjusted by an operator of device 10 based, at least in part, on a desired sampling region within the sampled tissue. Thus, a tissue sampling region may be determined by controlling an extent to which the multiple needles 32b spread outwardly with respect to a central longitudinal axis X of the device, thereby adjusting the device for use with target tissues of varying sizes and shapes.

Device 10 facilitates control of the position of, and suction through, needles 32b independently of that of needle 32a (as described in more detail hereinbelow). Additionally, or alternatively, if the physician desires, needle 32a may be used without using (e.g., without advancing) needles 32b (or vice versa).

In some embodiments, one or more anchoring features may be incorporated into needle 32a. In some embodiments, the anchoring features may be configured to engage the surrounding tissue to anchor and/or position at least needle 32a at a desired position within the body, and to prevent undesired migration of the device from the desired sampling site.

In some embodiments, anchoring and/or positioning features may include one or more of an inflatable member, e.g., a balloon; a suction feature; any gripping member; any retractable spike; one or more serrations; one or more threaded portions; one or more crossbar or T-bar anchors; and the like.

Reference is now made to FIGS. 9A-9B, which are schematic illustrations of a first central needle 32a, in accordance with some embodiments of the present invention. As described hereinabove, needle 32a is advanced into the target tissue prior to surrounding outer needles 32b. Typically, needle 32a is advanced into the target tissue to facilitate anchoring of device 10 in the target tissue, in addition to obtaining a tissue sample. In some embodiments, additionally or alternatively to having a lower gauge and/or a greater length than any one of outer needles 32b, needle 32a is shaped to define a side-facing anchoring-facilitating notch, port or aperture 102.

Figure 9C:
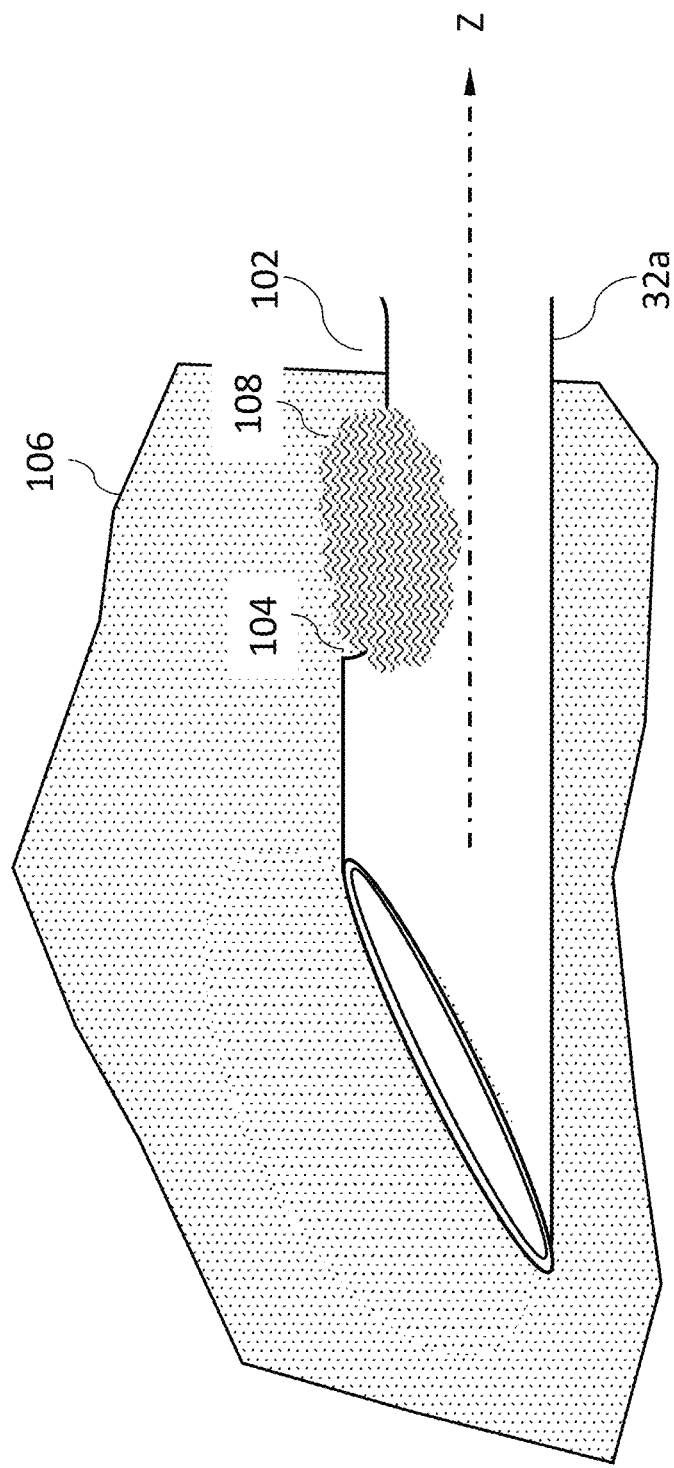

Typically, the side-facing port or aperture 102 is in communication with the lumen of the needle and has a proximally facing distal edge 104. As can be seen in FIG. 9C, when engaging the tissue, a portion 108 of the tissue 106 may prolapse into and/or received within port or aperture 102, wherein such prolapsed and/or received tissue portion 108 tends to restrain the needle from disengaging the tissue, e.g., through backward axial motion in the proximal direction indicated by arrow Z. In some embodiments, a distal edge or lip 104 of port or aperture 102 contacting the tissue portion 108 prolapsed and/or received within port or aperture 102, may act as a stop measure which tends to resist axial motion of needle 32a in the proximal direction marked by arrow Z. For example, when the distal edge or lip 104 is brought against the tissue portion 108 prolapsed and/or received within port or aperture 102. In some embodiments, distal edge or lip 104 of port or aperture 102 may define a relatively non-incisive edge which requires an application of a predetermined force in order to incise and/or sever a tissue prolapsed and/or received within port or aperture. Accordingly, typical forces tending to remove needle 32a from its anchoring position in the tissue 106 (e.g., the advancing into and engaging of tissue 106 of outer needles 32b), will not be sufficient to cause edge or lip 104 to incise the tissue portion 108 prolapsed and/or received within port or aperture 102. Conversely, when the operating physician is prepared to withdraw the needle from the tissue, a force which exceeds a predetermined threshold is manually applied by the physician in order to pull the needle proximally and remove it from the tissue. In some embodiments, such removal may cause an incision or severing to be made of tissue portion 108, such that an incised portion thereof may be further collected as a sample.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. An apparatus for sampling a target organ the apparatus comprising:
 a sheath, shaped to define a plurality of openings at a distal face of the sheath;
 an elongated first needle extendible perpendicularly from said distal face of said sheath through one of said plurality of openings, wherein said first needle comprises at least one anchoring element, comprising a side-facing aperture configured to receive, a portion of a tissue, located at a distal portion of said first needle, configured to prevent a migration of said apparatus from said target organ by receiving the portion of the tissue into the side-facing aperture, such that the portion of the tissue remains intact to the target organ during the anchoring; and
 an assembly comprising at least two second needles arranged in a predetermined pattern relative to said first needle, and extendible perpendicularly from said distal face of said sheath, wherein each of said second needles is extendible out of one of said plurality of openings, wherein, when extended from said distal face of said sheath:
 (i) each of said second needles extends a different length from said distal face of said sheath,
 (ii) at least a distal portion of each of said second needles is resiliently biased to extend laterally outwardly in relation to said first needle, and (iii) a lateral spread region defined by said distal portions of all of said second needles is determined based, at least in part, on a distance of said extending from said distal face of said sheath.

2. The apparatus according to claim 1, wherein said first needle and said assembly are each configured to be extendible independently of one another.

3. The apparatus according to claim 1, wherein said side-facing aperture is configured to receive a portion of said target organ therein, and wherein said side-facing aperture comprises a distal edge configured to incise said target organ only upon application of a predetermined amount of axial force.

4. The apparatus according to claim 1, wherein said predetermined pattern comprises said at least two second needles arranged in a surrounding pattern relative to said first needle.

5. The apparatus according to claim 1, further comprising a manipulating hub coupled to said sheath, wherein said manipulating hub comprises a first and second slide members configured to reciprocally slide distally and proximally along a common axis.

6. The apparatus according to claim 5, wherein:
(i) said reciprocal sliding of said first slide member is configured to reciprocally extend and retract said first needle from said distal face of said sheath; and
(ii) said reciprocal sliding of said second slide member is configured to reciprocally extend and retract said assembly from said distal face of said sheath.

7. The apparatus according to claim 5, wherein an extent of said reciprocal sliding of said second slide member in the distal direction is determined by an axial position of said first slide member.

8. The apparatus according to claim 5, wherein said reciprocal sliding of said second slide member in the distal direction is only possible following said reciprocal sliding of said first slide member in the distal direction.

9. The apparatus according to claim 5, wherein said manipulating hub comprises a stop located distally to said first slide member, wherein said stop determines a maximal said reciprocal sliding of said first slide member in the distal direction.

10. The apparatus according to claim 5, wherein at least a portion of said manipulating hub is selectively rotatable (i) in tandem with or (ii) relative to said sheath.

11. A method for sampling a target organ, comprising:
providing an apparatus comprising:
a sheath, shaped to define a plurality of openings at a distal face of the sheath;
an elongated first needle extendible perpendicularly from said distal face of said sheath through one of said plurality of openings, wherein said first needle comprises at least one anchoring element, comprising a side-facing aperture at a distal portion of said first needle, configured to prevent a migration of said apparatus from said target organ; and
an assembly comprising at least two second needles arranged in a predetermined pattern relative to said first needle, and extendible perpendicularly from said distal face of said sheath, wherein each of said second needles is extendible out of one of said plurality of openings,
wherein, when extended from said distal face of said sheath:
(i) each of said second needles extends a different length from said distal face of said sheath,
(ii) at least a distal portion of each of said second needles is resiliently biased to extend laterally outwardly in relation to said first needle, and
(iii) a lateral spread region defined by said distal portions of all of said second needles is determined based, at least in part, on a distance of said extending from said distal face of said sheath;
extending said first needle to engage said target side;
anchoring said first needle by receiving a portion of a tissue in the target side into the side-facing aperture, wherein the portion of the tissue remains intact to the target side during the anchoring; and
extending said assembly to engage said target side.

12. The method according to claim 11, wherein said first needle and said assembly are each configured to be extendible independently of one another.

13. The method according to claim 11, wherein said side-facing aperture comprises a distal edge configured to incise said target organ only upon application of a predetermined amount of axial force.

14. The method according to claim 11, wherein said predetermined pattern comprises said at least two second needles arranged in a surrounding pattern relative to said first needle.

15. The method according to claim 11, wherein said apparatus further comprises a manipulating hub coupled to said sheath, wherein said manipulating hub comprises a first and second slide members configured to reciprocally slide distally and proximally along a common axis.

16. The method according to claim 15, wherein:
(i) said reciprocal sliding of said first slide member is configured to reciprocally extend and retract said first needle from said distal face of said sheath; and
(ii) said reciprocal sliding of said second slide member is configured to reciprocally extend and retract said assembly from said distal face of said sheath.

17. The method according to claim 15, wherein an extent of said reciprocal sliding of said second slide member is determined by an axial position of said first slide member.

18. The method according to claim 15, wherein said manipulating hub comprises a stop located distally to said first slide member, wherein said stop determines a maximal said reciprocal sliding of said first slide member in the distal direction.

* * * * *